United States Patent [19]

Joncour et al.

[11] Patent Number: 4,626,088

[45] Date of Patent: Dec. 2, 1986

[54] OCULAR PARAMETER MEASURING DEVICE WITH DIGITALLY CONTROLLED VIRTUAL GRATICULES

[75] Inventors: Christian Joncour, Villeneuve-Saint-Georges; Alain Pierre, Paris; Patrice Renan, Paris; Jean-Louis Roumegoux, Paris; Francoise Richard, deceased, late of Joisin-le-Bretonneux; by Jacques M. G. Richard, heir, Cugnaux; Alexandra A. C. Richard, heir, Cugnaux; Anne-Lise P. M. Richard, heir, Cugnaux, all of France

[73] Assignee: Essilor International Cie Generale d'Optique, Creteil, France

[21] Appl. No.: 683,389

[22] Filed: Dec. 19, 1984

[30] Foreign Application Priority Data

Dec. 29, 1983 [FR] France ................................ 83 21010

[51] Int. Cl.⁴ .............................................. A61B 3/10
[52] U.S. Cl. ...................................... 351/204; 33/200
[58] Field of Search ........................... 351/204; 33/200

[56] References Cited

U.S. PATENT DOCUMENTS 4,092,567 5/1978 Sharrit .

FOREIGN PATENT DOCUMENTS 1211813 3/1966 Fed. Rep. of Germany .
2623093 9/1977 Fed. Rep. of Germany .
2910022 7/1980 Fed. Rep. of Germany .
931377 2/1948 France .
1506352 12/1967 France .

*Primary Examiner*—Rodney B. Bovernick
*Attorney, Agent, or Firm*—Charles E. Brown; Charles A. Brown

[57] ABSTRACT

A device for measuring a subject's ocular parameters, in particular the interpupillary distance, comprises a front plate against which the face of the subject is placed, comprising two windows substantially corresponding to the lenses of a pair of eyeglasses. A lens is movable along its optical axis, which is perpendicular to the front plate, from an origin position near the front plate. A viewing eyepiece is disposed at the focus of the lens when in the origin position. A semi-reflecting mirror disposed at 45° renders the eyepiece and a point source coincident, as far as the subject is concerned. Parallel to the semi-reflecting mirror, another mirror reflects an image of a cathode ray tube screen to the eyepiece through another lens. Adjustable calibrated voltage sources are used to produce coincidence of the reflections of the source on the corneas of the eyes of the subject and the luminous traces on the screen of the cathode ray tube, as seen by an operator looking through the eyepiece. These traces constitute graticules, and the voltages which generate them constitute basic measurements of the ocular parameters. The appropriate calculations are implemented by a microprocessor.

8 Claims, 3 Drawing Figures

OCULAR PARAMETER MEASURING DEVICE WITH DIGITALLY CONTROLLED VIRTUAL GRATICULES

BACKGROUND OF THE INVENTION

1. Field of the Invention

The invention concerns a device for measuring a subject's ocular parameters, in particular the interpupillary distance, for the purposes of fitting a pair of eyeglasses.

2. Description of the prior art

When fitting a person with a pair of eyeglasses the lenses must be fitted in the frame so that their principal optical axes coincide with the optical axes of the corresponding eyes under average conditions of use. The frame acts as a secondary positional reference for the lenses, its position relative to the face of the person being essentially defined by the nose pads bearing on the opposite sides of the bridge of the nose and secondarily by the side pieces bearing on the ears.

The position of the lenses relative to the frame is conveniently defined in cartesian axes with a horizontal (relative to the face of the person) axis of abscissae and a vertical axis of ordinates, through the abscissa and the ordinate of the optical center of the lens. The origin of abscissae is naturally situated in the vertical plane of symmetry of the frame. For reasons of convenience in finishing the lenses, there is generally selected as the origin of the ordinates the horizontal straight line which passes through the bottom part of the frame hoops so that the ordinate is the distance between the optical center of the lens and its bottom edge.

The reader is reminded that the interpupillary distance is the distance between the optical axes of the eyes when focussed at infinity. The (vector) difference between the abscissae of the optical centers of the lenses must correspond to the interpupillary distance of the person.

French Pat. No. 1 506 352, filed Aug. 4 1966, describes an improved device for measuring the interpupillary distance by determining for each eye the position of the reflection on the cornea of a luminous point situated at infinity, with the gaze focussed at infinity. Analogous determinations are made with the gaze focussed on a point at a finite distance, in which case the optical axes of the eyes converge.

The device of the aforementioned patent essentially comprises a box in which there are disposed a lens which can be moved parallel to itself along its principal optical axis, a light source at the focus of the lens when the latter is at an origin position farthest removed from the source, this being offset geometrically from the optical axis by means of a semi-reflecting mirror disposed at 45°, and on two opposite sides of the box, perpendicular to the optical axis of the lens, an eyepiece situated on the optical axis at the focus of the lens in the origin position and a front plate comprising nose pads and two openings to simulate an eyeglass frame. The openings surround the intended location of the lenses and are provided with mobile markers forming graticules. For taking the measurements the mobile markers are made to coincide with the reflections of the point source on the corneas, as seen through the eyepiece. It will be noted that the position of the lens defines a virtual distance from the point source for the subject whereas the point from which the operator looks through the eyepiece is continuously coincident optically with the point source. Measuring the interpupillary distance for a gaze convergent to a near virtual point does not introduce any angular parallax error and the position of the graticule in the plane of the windows, which corresponds to the general plane of the lenses, defines the required position of the optical center of the lenses.

while the optical design of this device is excellent, the device suffers from imperfections in respect of the mechanical part controlling the displacement of the graticules. The necessary precision of a few tenths of a millimeter imposes the use of micrometer screws or racks for displacing the indexes, resulting in devices which are fragile and slow to operate. The position readings are difficult, involving verniers or drums associated with linear scales as soon as the precision required exceeds one half-millimeter. Furthermore, displacement of the graticules in two mutually perpendicular directions seriously complicates the mechanical control and display arrangements. In fact, the device as described in the aforementioned patent comprises only horizontally displaceable indexes, for determining principally the interpupillary distance and secondarily the distance of the eyeglass frame from the eye, by viewing in profile.

An object of the invention is a device for measuring ocular parameters capable of quickly producing precise data for matching lenses in an eyeglass frame to the ocular parameters of a person.

Another object of the invention is a device of this kind which provides, in addition to the interpupillary distances between the pupils and between each pupil and the axis of symmetry of the frame, the distance between the pupil and the lower edge of the frame, and which materializes the position of the lenses in the frame.

A further object of the invention is a device of this kind which produces directly usable numerical data.

SUMMARY OF THE INVENTION

The invention consists in a device for measuring a subject's ocular parameters, in particular the interpupillary distance, for the purposes of fitting a pair of eyeglasses, said device comprising a generally plant front plate, means for marking the position of the subject relative to said front plate, windows in said front plate corresponding to the locations of the lenses of the eyeglasses, optical means having an optical axis normal to and centered on said front plate comprising a convergent lens, a point light source and a viewing eyepiece optically coincident with said source on said optical axis, said optical means being on the opposite side of said convergent lens and the focus thereof when said convergent lens is at an origin position to said front plate, high-resolution luminous display means having a screen adapted to display graticules, optical coupling means whereby an image of said graticules is formed in the plane of said front plate and within the boundaries of said windows, deflection means comprising respective deflection circuits whereby the positions of said graticules within said windows may be adjusted vertically and horizontally, and means for displaying the position of said graticules.

The luminous display means are typically a cathode ray tube. It is known that the position of the light point or spot corresponding to the impact of the beam of electrons in a cathode ray tube on the light-emitting phosphor is precisely and repeatably conditioned by the values of signals applied to the horizontal and vertical deflection circuits connected to the tube. It will have been understood that, for the observer looking through the viewing eyepiece, the opical coupling means renders the image of the front plate with the face of the subject coincident with the image of the cathode ray tube screen. To evaluate the position of the center of the pupil relative to the front plate, it is then merely necessary to operate on the defelection system control signals in order to bring the image of the cathode ray tube spot over the reflection of the point source on the corneas of the eyes of the subject, which are focussed on the image of the point source through the lens, and to note the magnitude of the signals necessary to obtain this coincidence. This measurement does not employ any material mobile marker device. The techniques of digital control, especially when a microprocessor is used, provide for the precise and rapid adaptation of the deflection control signals and the expression of the values of the ocular parameters.

It will be understood that the optical coupler maintains the graticules outside the visual field of the subject. Thus, unlike prior art arrangements, adjusting the graticules does not entail the risk of provoking reflex movements of the eyes of the subject.

Other objects and advantages will appear from the following description of an example of the invention, when considered in connection with the accompanying drawings, and the novel features will be particularly pointed out in the appended claims.

DESCRIPTION OF THE PREFERRED EMBODIMENT

Figure 1:
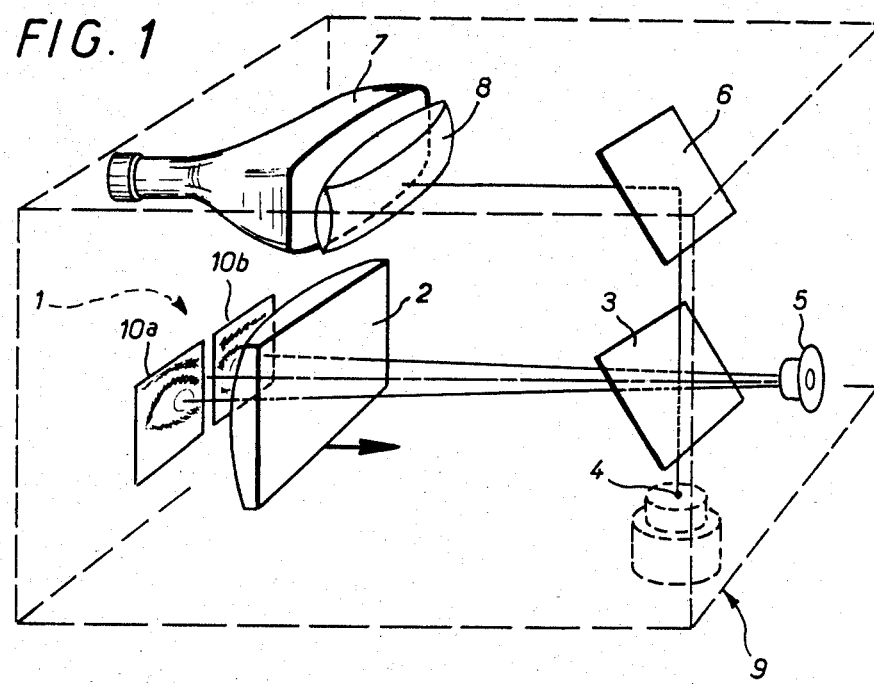
FIG. 1 is a schematic view in perspective of a measuring device in accordance with the invention.
Figure 2:
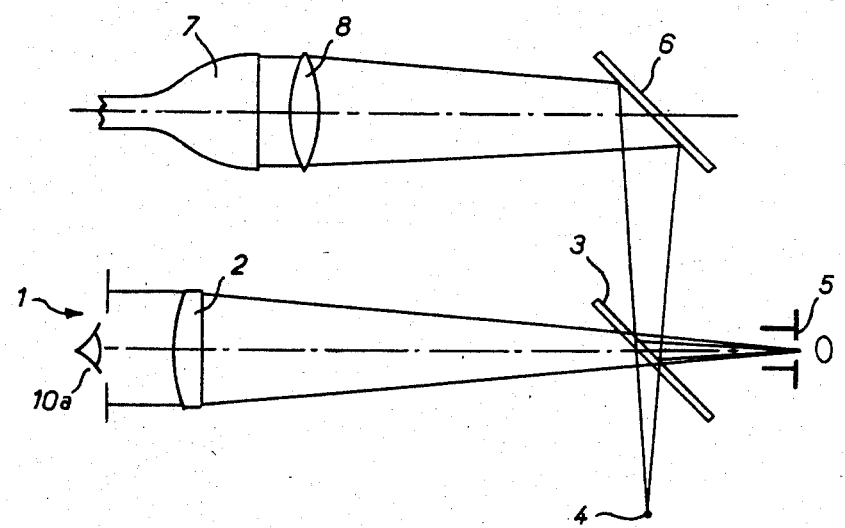
FIG. 2 is a light ray schematic.
Figure 2:
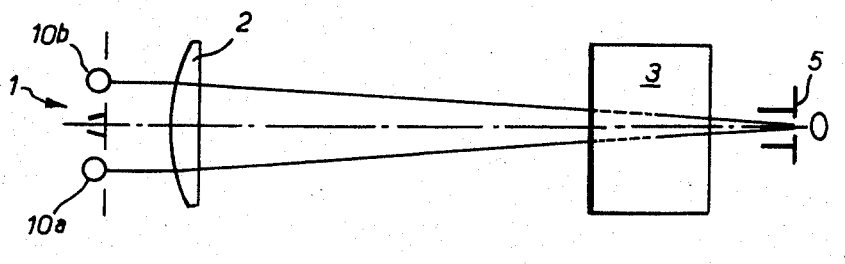

In the selected embodiment represented in FIGS. 1 and 2 the optical part proper of the ocular parameter measuring device comprises a rectangular box 9 with a front plate 1 in which there are two windows 10a and 10b which correspond to the average locations of the lenses of the eyeglasses of a person whose face is applied against the outside of the front plate 1. It will be understood that this front plate comprises nose plates, and possibly other shaped parts, so that the measurements taken on the person using the apparatus are applicable without error to the eyeglasses which the person will wear.

A planoconvex lens 2 is disposed in the apparatus with its optical axis perpendicular to the plane of the front plate 1 and passing through this plane between the windows 10a and 10b, substantially at the mid-height of the latter. On the side of the box 9 opposite the front plate 1, and centered on the optical axis of the lens 2, there is disposed an eyepiece 5 for the operator. The lens 2 is mobile in translation along its optical axis, from an origin position near the front plate 1 at which the focus of the lens 2 is located at the center of the eyepiece 5.

It will be noted that adjustment of the position of the lens 2 is necessary only when it is necessary to determine with accuracy geometric features of lenses for a long sighted person. Even in this case adjustment of the position of the lens is in relation to second order corrections which are generally negligible.

Also, the lens 2 may be biconvex or concave-convex, the factors determining its shape being optical quality and cost.

On the optical axis of the lens 2 there is disposed a semi-reflecting mirror 3 inclined at 45° to the horizontal. A point light source 4 is disposed beneath the mirror 3 so that for an observer at the location of the subject the source 4 and the eyepiece 5 are conjugate and appear coincident. When the lens 2 is at its origin position, the subject will be see the source 4 as a point at infinity in front of him. For the operator looking throught the eyepiece 5, the reflections of the source 4 on the corneas of the eyes of the subject appear as two luminous points, each at the center of one pupil when the subject focusses on the image of the source. It will be noted that when the lens 2 moves away from the front plate 1, and thus away from its origin position, the subject will see the image of the source 4 coming closer, its apparent distance being determined according to known laws of geometrical optics. For the operator, however, the reflections of the soruce 4 in the corneas of the eyes of the subject will remain centered in the pupil.

The reader is reminded that all this part of the apparatus for measuring ocular parameters is well known from French Pat. No. 1 506 352.

Parallel to the semi-reflecting mirror 3 there is disposed a mirror 6 with its center aligned with the center of the mirror 3 and the source 4. On a secondary optical axis parallel to the optical axis of the lens 2 and passing through the center of the mirror 6 there are disposed a convergent lens 8 and the flat screen of a measuring cathode ray tube 7, perpendicular to the secondary optical axis. The focus of the lens 8 coincides, after reflection from the mirror 6 and passing through the mirror 3, with the source 4 and, after double reflection from the mirror 6 and the mirror 3, with the center of the eyepiece 5. The combination of the lens 8 and mirror 6 forms with the semi-reflecting mirror 3 an optical coupler.

As a result, for the opeator looking through the eyepiece 5, the image of the front plate 1 and that of the screen of the cathode ray tube 7 are coincident, with relative enlargement determined by the ratio of the focal lengths of the lense 2 and 8, which are known. It is therefore possible to determine the coordinates of any point on the front plate 1 in the area of the windows 10a and 10b by producing coincidence, for the operator looking through the eyepiece 5, of the point in question and the trace of the impact of the electron beam on the screen of the tube 7, by measured action on the deflection means.

For the subject, on the other hand, the screen of the cathode ray tube 7 remains invisible. This avoids reflex movement of the eyes of the subject provoked by displacements of the graticules in the subject's visual field. In prior art devices the graticules are perceivable as vague shapes, even though they lie well away from the punctum proximum.

Figure 3:
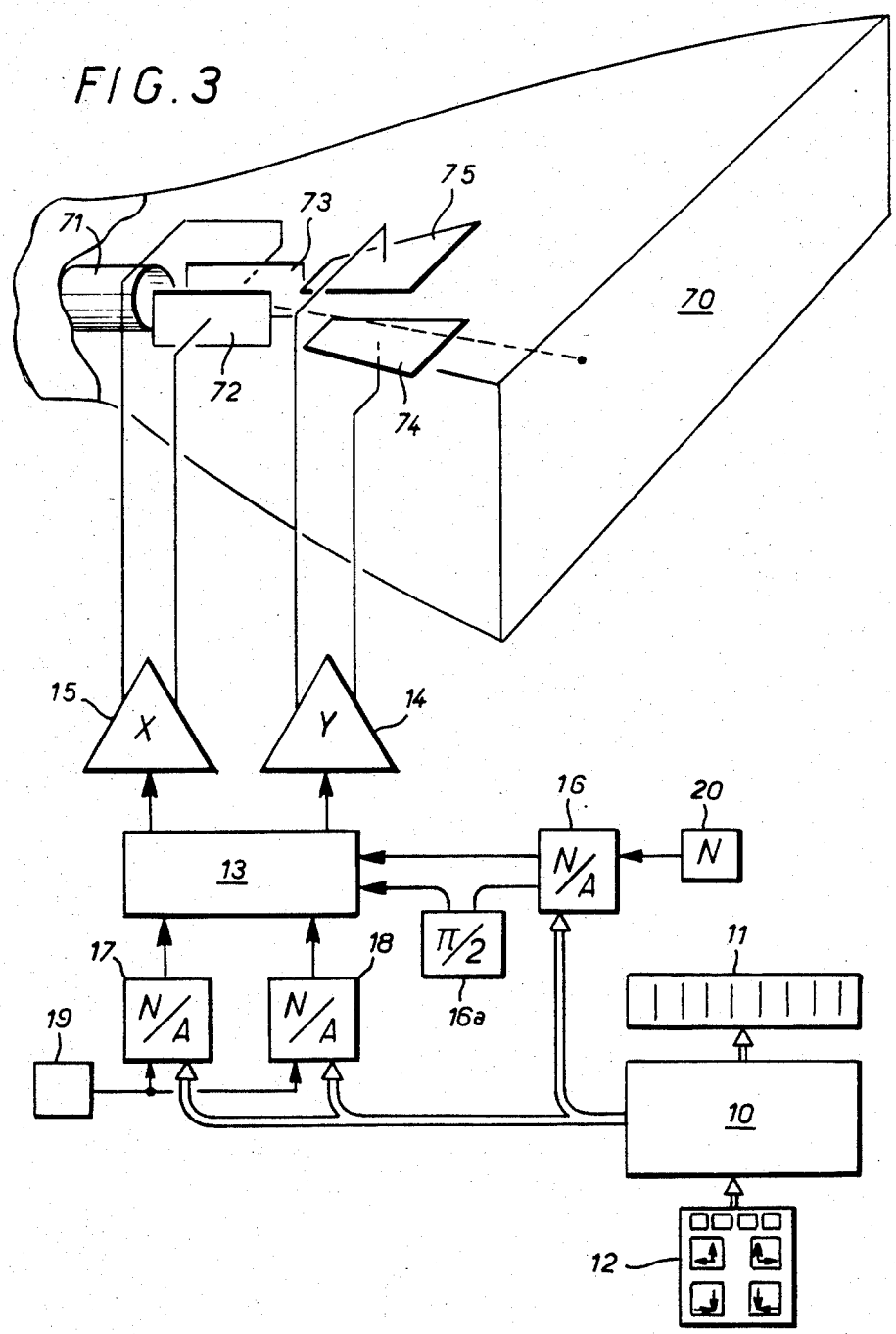
FIG. 3 is a schematic of the circuits controlling the cathode ray tube.

FIG. 3 represents the control means for forming on the screen 70 of the cathode ray tube 7 the luminous traces which correspond to the graticules of conventional ocular parameter measuring devices.

The tube 7 is a measuring cathode ray tube with flat high-definition rectangular screen and electrostatic deflection featuring, in succession in the direction away from an electron gun 71, a pair of horizontal deflection plates 72, 73 and a pair of vertical deflection plates 74, 75.

The electric fields at deflection pairs 72, 73 and 74, 75 are obtained from the outputs of respective deflection amplifiers 15 and 14 driven by respective outputs of a combiner switch 13. This combiner switch receives voltages from digital-to-analog converters 17 and 18 connected to a common reference voltage source 19 and a pair of voltages from a digital-to-analog converter 16, one directly and the other via a phase-shifting circuit 16a. To the reference input of the converter 16 there is applied a sinusoidal voltage from a generator 20 with a frequency such that the phase shift introduced by the circuit 16a is $\pi/2$. The combiner switch 13 functions so that the voltage applied to the amplifier 15 is proportional to the sum of the voltages obtained directly from the converter 16 and from the converter 17 whereas the voltage applied to the amplifier 14 is proportional to the sum of the voltages obtained from the converter 18 and from the converter 16 via the phase shifter 16a.

A microprocessor 10 associated with a control keyboard 12 and a display unit 11 periodically feeds digital signals to the converters 16, 17 and 18. When there is no digital signal at the input of the converter 16, the conjoint digital signals at the converters 17 and 18 respectively define an abscissa and an ordinate for the point of impact of the electron beam on the screen 70 of the tube 7. If the converters 17 and 18 receive two pairs of digital signals in alternation, two luminous points will be seen on the screen. By varying these pairs of digital signals, principally the digital signals addressed to the converter 17 controlling the horizontal deflection, the two traces can be overlaid on the two reflections on the corneas of the two eyes of the subject. The interpupillary distance will be a function of the difference between the values of the two digital signals addressed alternately to the converter 17. It will be noted that it is also possible to determine if the centers of the pupils are offset in the vertical direction.

With four pairs of signals in sequence it is possible to obtain four reference points; two pairs will be assigned, as previously, to the coincidence of the spots with the reflections on the corneas of the two eyes of the subject, and the other two pairs will be associated with traces brought into coincidence with the base of a frame. The differences between the signals applied to the converter 18 of the first and third and then second and fourth pairs will define the distance between the optical centers of the lenses and the corresponding bases of the frames.

Moreover, two triplets of signals may be applied to the converters 16, 17 and 18, either alternately with the foregoing signals or in substitution therefore. The digital signal applied to the digital-to-analog converter 16 results in the appearance at the corresponding inputs of the switch 13 of two sinusoidal voltages in phase quadrature and of the same amplitude, determined by the value of the digital signal applied to the converter 16. The corresponding trace on the screen 70 is a circumference of radius determined by the amplitude of the signals in phase quadrature. The reception of two digital signals by the converters 17 and 18 for a duration at least equal to one period of the sinusoidal signal delivered by the generator 20 determines values of polarization of the signals addressed to the amplifiers 14 and 15, in other words the coordinates of the center of a circle, the radius of which is determined by the digital signal applied to the converter 16. The alternation of the two triplets of digital signals forms an image of two eyeglass lenses the position of which on the actual face of the subject can be adjusted at will.

It goes without saying that the microprocessor processes the data which it delivers to the three digital-to-analog converters 16, 17 and 18 so as to display on the display unit 11, and possibly record on an appropriate medium, all output data usable for adjusting the frame and lenses of a pair of eyeglasses. Everything relating to the generation and processing of data by the microprocessor 10 and its control by the keyboard 12 is within the competence of a man skilled in the art and outside the scope of the present invention. For clarity of descriptin there is no need to describe in detail the particular features of the software, given that the characteristics of the output signals are functionally defined.

It will also be clear that the power supply to the cathode ray tube may be achieved by conventional means, requiring no further explanation. In particular, the control of the variation with time in the intensity of the electron beam as a function of the nature of the signals applied to the deflection means 72-75 will not be described in detail, but it goes without saying that the blanking of signal transitions and the adjustment for balanced brightness are implemented in an appropriate manner.

The foregoing description has made reference to a cathode ray tube on the screen of which the graticules are displayed. It goes without saying that this cathode ray tube may be replaced by any equivalent high-resolution luminous display means for converting control voltages into displacements of the image of a point.

More generally, it will be understood that various changes in the details, materials and arrangements of parts which have been herein described and illustrated in order to explain the nature of the invention may be made by those skilled in the art within the principle and scope of the invention as expressed in the appended claims.

What we claim is:

1. Device for measuring a subject's ocular parameters, in particular the interpupillary distance, for the purposes of fitting a pair of eyeglasses, said device comprising a generally plane front plate, means for marking the position of the subject relative to said front plate, windows in said front plate corresponding to the locations of the lenses of the eyeglasses, optical means having an optical axis normal to and centered on said front plate comprising a convergent lens, a point light source and a viewing eyepiece optically coincident with said source on said optical axis, said optical means being on the opposite side of said convergent lens and the focus thereof when said convergent lens is at an origin position to said front plate, high-resolution luminous display means having a screen adapted to display graticules, optical coupling means whereby an image of said graticules is formed in the plane of said front plate and within the boundaries of said windows, deflection means comprising respective deflection circuits whereby the positions of said graticules within said windows may be adjusted vertically and horizontally, and means for displaying the position of said graticules.

2. Device according to claim 1, wherein said luminous display means comprise a cathode ray tube.

3. Device according to claim 1, wherein said optical coupling means comprise a second convergent lens and two parallel mirrors adapted to align the optical axis of said second convergent lens with that of the device and to render the focus of said second convergent lens coincident with that of the first-mentioned convergent lens when the latter is in said origin position.

4. Device according to claim 3, wherein said mirrors are inclined at 45° to the optical axes of said first-mentioned and second convergent lenses, a first of said mirrors is located on the optical axis of the device and is a semi-reflecting mirror and said point light source is disposed on the side of said first mirror opposite the second of said mirrors and aligned with the optical axis between said mirrors.

5. Device according to claim 1, further comprising a microprocessor having digital outputs connected to said deflection means and to said display means.

6. Device according to claim 5, wherein said deflection means comprise at least two digital-to-analog converters connected to respective deflection circuits.

7. Device according to claim 6, wherein said deflection means further comprise a sinusoidal signal generator the output level of which is controlled by said microprocessor and having two outputs in phase quadrature connected to respective deflection circuits.

8. Device according to claim 7, wherein said digital-to-analog converter and said signal generator are additively coupled to each deflection circuit.

* * * * *